US010363163B2

(12) United States Patent
Nazzaro et al.

(10) Patent No.: US 10,363,163 B2
(45) Date of Patent: Jul. 30, 2019

(54) INJECTOR APPARATUS

(71) Applicant: pSivida US, Inc., Watertown, MA (US)

(72) Inventors: Martin Nazzaro, Quincy, MA (US); Josh York, Ipswich, MA (US); Ron Leblanc, Hopedale, MA (US)

(73) Assignee: EYEPOINT PHARMACEUTICALS, INC., Watertown, MA (US)

( * ) Notice: Subject to any disclaimer, the term of this patent is extended or adjusted under 35 U.S.C. 154(b) by 726 days.

(21) Appl. No.: 14/850,374

(22) Filed: Sep. 10, 2015

(65) Prior Publication Data

US 2016/0074213 A1 Mar. 17, 2016

Related U.S. Application Data

(60) Provisional application No. 62/048,902, filed on Sep. 11, 2014.

(51) Int. Cl.
*A61F 9/00* (2006.01)
*A61M 5/32* (2006.01)
*A61M 37/00* (2006.01)

(52) U.S. Cl.
CPC ........... *A61F 9/0008* (2013.01); *A61M 5/322* (2013.01); *A61M 37/0069* (2013.01); *A61M 2005/3228* (2013.01)

(58) Field of Classification Search
CPC .......... A61M 2005/3201; A61M 5/322; A61M 5/3221; A61M 2005/3228; A61M 5/3287; A61M 37/0069; A61M 2005/3223; A61M 2005/3224; A61M 2005/3226; A61M 5/3232; A61M 5/3291; A61F 9/0008
See application file for complete search history.

(56) References Cited

U.S. PATENT DOCUMENTS

| | | | |
|---|---|---|---|
| 3,094,121 A | 6/1963 | Blumenstein et al. | |
| 3,483,810 A | 12/1969 | Peters | |
| 4,105,030 A | 8/1978 | Kercso | |
| 4,810,244 A | 3/1989 | Allen | |
| 4,820,267 A * | 4/1989 | Harman | A61M 37/0069 604/60 |
| 4,871,094 A | 10/1989 | Gall et al. | |
| 4,944,728 A | 7/1990 | Carrell et al. | |
| 4,994,028 A * | 2/1991 | Leonard | A61M 37/0069 604/59 |
| 5,057,082 A | 10/1991 | Burchette, Jr. | |
| 5,250,026 A | 10/1993 | Ehrlich et al. | |
| 5,273,532 A | 12/1993 | Niezink et al. | |

(Continued)

FOREIGN PATENT DOCUMENTS

| | | |
|---|---|---|
| CN | 101596337 A | 12/2009 |
| DE | 10 2008 006 602 A1 | 7/2009 |

(Continued)

OTHER PUBLICATIONS

International Search Report dated Jan. 20, 2016 in PCT/US2015/049389.

(Continued)

*Primary Examiner* — Shefali D Patel
(74) *Attorney, Agent, or Firm* — Hogan Lovells US LLP

(57) ABSTRACT

The devices and methods described herein relate to injector devices for delivering payloads to a tissue.

48 Claims, 2 Drawing Sheets

(56) References Cited

U.S. PATENT DOCUMENTS

| | | | |
|---|---|---|---|
| 5,284,479 A * | 2/1994 | de Jong | A61M 37/0069 604/130 |
| 5,370,630 A | 12/1994 | Smidebush et al. | |
| 5,792,099 A | 8/1998 | DeCamp et al. | |
| 6,375,972 B1 * | 4/2002 | Guo | A61K 9/0051 424/422 |
| 7,090,681 B2 | 8/2006 | Weber et al. | |
| 7,468,065 B2 | 12/2008 | Weber et al. | |
| 7,798,988 B2 | 9/2010 | Aubert et al. | |
| 7,976,490 B2 | 7/2011 | Lawler et al. | |
| 8,131,346 B2 | 3/2012 | Chesbrough et al. | |
| 2003/0004457 A1 | 1/2003 | Andersson | |
| 2003/0093084 A1 | 5/2003 | Nissan et al. | |
| 2004/0199140 A1 | 10/2004 | Rue et al. | |
| 2004/0230183 A1 | 11/2004 | Breegi et al. | |
| 2004/0243101 A1 | 12/2004 | Gillis | |
| 2004/0260300 A1 | 12/2004 | Gorensek et al. | |
| 2005/0101967 A1 * | 5/2005 | Weber | A61F 2/167 606/107 |
| 2006/0111605 A1 | 5/2006 | Larsen et al. | |
| 2006/0235430 A1 | 10/2006 | Le et al. | |
| 2007/0073248 A1 | 3/2007 | Moenning | |
| 2007/0073265 A1 | 3/2007 | Rue et al. | |
| 2007/0191863 A1 | 8/2007 | De Juan et al. | |
| 2008/0195135 A1 | 8/2008 | Attinger | |
| 2008/0281292 A1 | 11/2008 | Hickingbotham et al. | |
| 2009/0281520 A1 | 11/2009 | Highley et al. | |
| 2009/0299298 A1 | 12/2009 | Bussmann | |
| 2010/0234817 A1 * | 9/2010 | Nazzaro | A61B 17/3468 604/272 |
| 2012/0016572 A1 | 1/2012 | Maas et al. | |
| 2012/0041369 A1 * | 2/2012 | Becker | A61M 5/329 604/117 |
| 2012/0165723 A1 | 6/2012 | Horvath et al. | |

FOREIGN PATENT DOCUMENTS

| | | |
|---|---|---|
| EP | 0239244 A1 | 2/1987 |
| EP | 3596162 A1 | 5/1994 |
| EP | 3639387 A1 | 2/1995 |
| JP | S62201159 A | 9/1987 |
| JP | S63-35261 A | 2/1998 |
| JP | 2001-502937 A | 3/2001 |
| JP | 2003-509082 A | 3/2003 |
| JP | 2003530964 A | 10/2003 |
| JP | 2005-533619 A | 11/2005 |
| JP | 2006-320736 A | 11/2006 |
| JP | 2006-525953 A | 11/2006 |
| JP | 2008-508916 A | 3/2008 |
| JP | 2012517323 A | 8/2012 |
| WO | 94/11042 A1 | 5/1994 |
| WO | 99/53991 A1 | 10/1999 |
| WO | 200074750 A2 | 12/2000 |
| WO | 2004/026106 A2 | 4/2004 |
| WO | WO-2005/053774 A1 | 6/2005 |
| WO | 2007/142890 A2 | 12/2007 |
| WO | 2008/033426 A1 | 3/2008 |
| WO | 2008/070402 A2 | 6/2008 |
| WO | 2008/088623 A2 | 7/2008 |

OTHER PUBLICATIONS

Communication dated Mar. 26, 2018 issued in EP Application No. 15840278.4.

Office Action dated Apr. 23, 2019 for JP Patent Application No. 2017-513390.

* cited by examiner

INJECTOR APPARATUS

CROSS-REFERENCE TO RELATED APPLICATIONS

This application claims the benefit of U.S. Provisional Application No. 62/048,902, filed on Sep. 11, 2014, which is incorporated herein by reference in its entirety.

BACKGROUND

A primary difficulty in treating diseases of the eye is introducing drugs or therapeutic agents into the eye and maintaining these drugs or agents at a therapeutically effective concentration in the eye for the necessary duration of a treatment. Systemic administration may not be an ideal solution because, often, unacceptably high levels of systemic dosing are needed to achieve effective intraocular concentrations, which increases the incidence of unacceptable side effects of the drugs. Simple ocular instillation or application is not an acceptable alternative in many cases, because the drug may be quickly washed out by tear-action or pass from the eye into the general circulation. Suprachoroidal injections of drug solutions have also been performed, but again, the drug availability is short-lived. Such methods make it difficult to maintain therapeutic levels of a drug in the eye for adequate time periods.

Efforts to address this problem have led to the development of drug delivery devices, or implants, which can be implanted into the eye such that a controlled amount of a desired drug can be released constantly over a period of several days, or weeks, or even months. Many such devices have been reported. But efficient, reliable injection with an acceptable level of patient discomfort can still be difficult to achieve.

A more facile, convenient, less invasive, and/or less traumatic means for delivering implants into the eye would be desirable.

SUMMARY OF THE INVENTION

The present invention discloses injector devices for delivering payloads to a tissue in which the device pierces the tissue to position a cannula through which the payload may be delivered. The prior art describes devices that utilize a solid trocar to pierce a tissue (see, for example, U.S. Pat. No. 8,192,408). Solid trocars were thought to be necessary because the lumen of a needle may core the tissue, for example, by cutting a cylindrical section of the tissue that enters the needle's lumen. Loss of this piece of the sclera could cause leakage from the injection site and slow healing, potentially leading to further complications. Nevertheless, the devices disclosed herein use needles instead of solid trocars to puncture the sclera. In certain embodiments, these devices permit the delivery of payloads to human patients with significantly less pain and discomfort than corresponding devices with solid trocars.

DETAILED DESCRIPTION OF THE INVENTION

Figure 1:
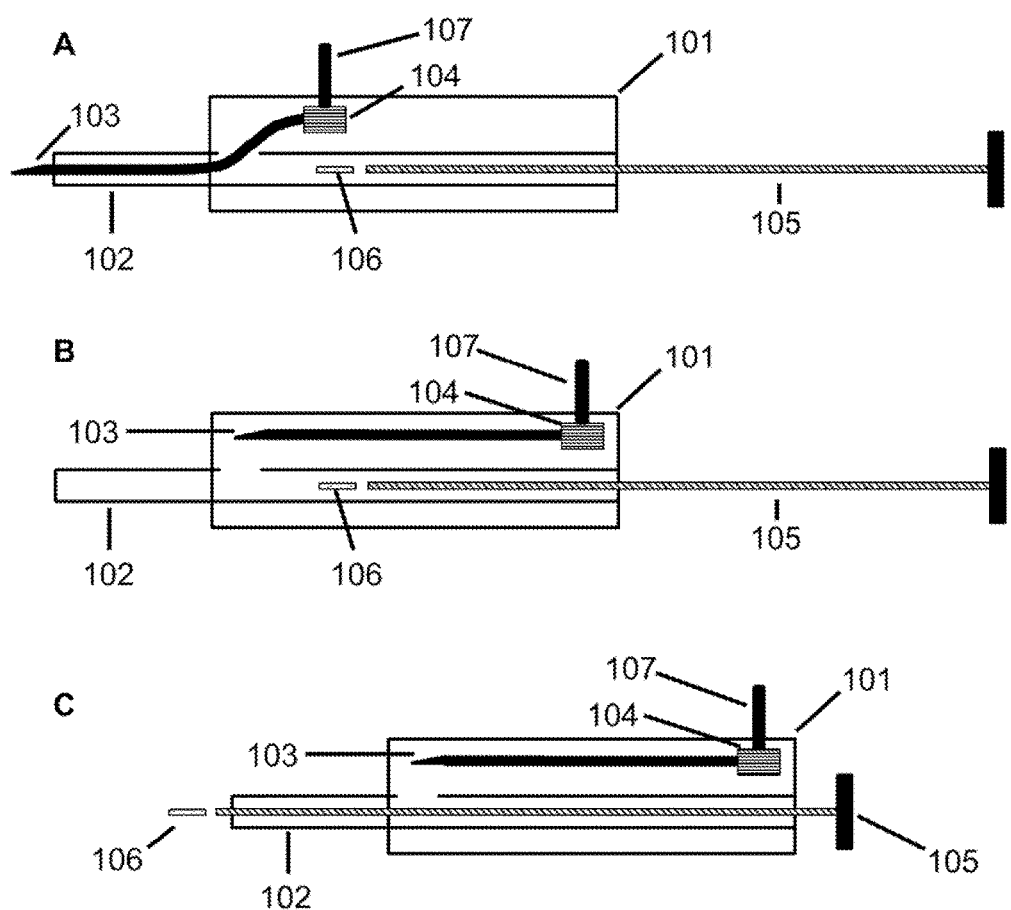
FIG. 1 depicts the injector device according to one embodiment of the present invention. 1A depicts an injector device with the needle 103 in an extended position and the payload 106 in an initial position. 1B depicts an injector device with the needle 103 in a retracted position. 1C depicts an injector device wherein the payload 106 has advanced from an initial position to exit from the distal end of the cannula 102.

An embodiment of the injector device of the present invention is depicted in FIG. 1. As shown, the injector device includes a housing 101 with a cannula 102 and needle 103 that extend outside of the housing 101. The cannula 102 defines a lumen and has a proximal portion received in the housing 101 and a distal portion extending from the housing 101. The cannula 102 may be integral to or separate from the housing 101. The needle 103 comprises a distal end with a tip for piercing tissue and a proximal end in communication with a shifter 104 for positioning the needle 103.

FIG. 1A depicts the needle 103 in an extended position, wherein the needle 103 occupies at least part of the lumen of the cannula 102 and the needle 103 is positioned to pierce a tissue. The injector device optionally includes a plunger 105 disposed in the lumen defined by the cannula 102. The plunger's shape may vary as long as it fits into the lumen defined by the cannula 102. The injector device may optionally comprise a payload 106, wherein the payload 106 comprises a therapeutically effective amount of one or more drugs. The injector device may optionally comprise a latch 107, wherein the latch 107 is located on the exterior of the housing 101, the latch 107 is coupled to the shifter 104, and the latch 107 allows a user to retract the needle 103 from the extended position to the retracted position.

FIG. 1B depicts an embodiment of the injector device in which the needle 103 is in a retracted position, wherein the needle 103 is withdrawn from the lumen of the cannula 102 sufficiently to permit a payload 106 to advance from an initial position through the distal end of the cannula 102. As shown, the injector device includes a housing 101, shifter 104, plunger 105, and latch 107.

FIG. 1C depicts an embodiment of the injector device in which the needle 103 is in a retracted position and the plunger 105 has advanced a payload 106 from an initial position through the distal end of the cannula 102. As shown, injector device includes a housing 101, shifter 104, and latch 107.

Figure 2:
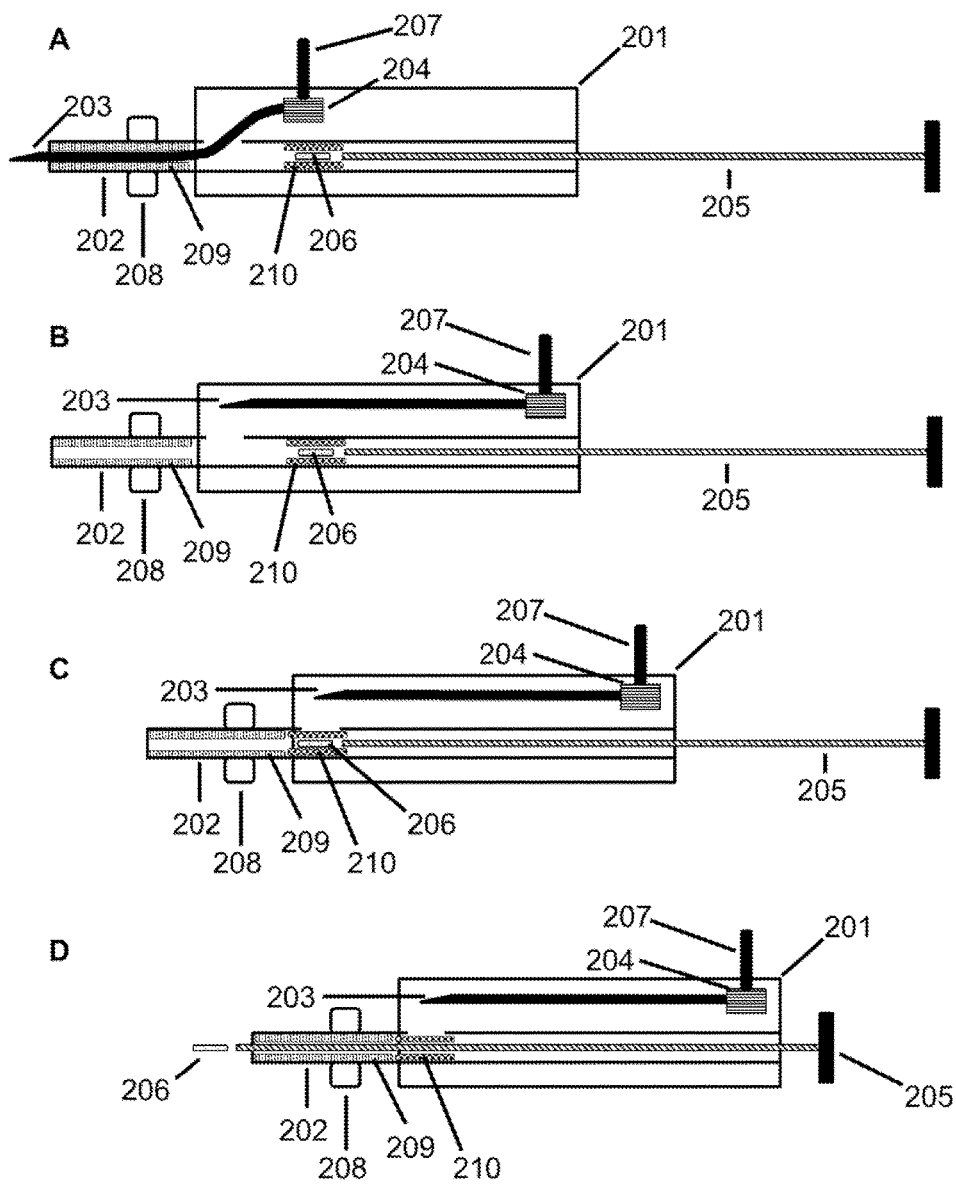
FIG. 2 depicts the injector device according to one embodiment of the present invention with a stop 208, a sheath 210, and a catch 209. 2B depicts an injector device according to one embodiment of the present invention with the needle 203 in a retracted position. 2C depicts an injector device, wherein the catch 209 prevents the sheath 210 from advancing through the distal end of the cannula 202. 2D depicts an injector device, wherein the payload 206 has advanced from an initial position to exit from the distal end of the cannula 202.

An embodiment of the injector device of the present invention is depicted in FIG. 2. As shown, the injector device includes a housing 201 with a cannula 202 and needle 203 that extend outside of the housing 201. The cannula 202 defines a lumen and has a proximal portion received in the housing 201 and a distal portion extending from the housing 201. The cannula 202 may be integral to or separate from the housing 201. The needle 203 comprises a distal end with a tip for piercing tissue and a proximal end in communication with a shifter 204 for positioning the needle 203.

FIG. 2A depicts the needle 203 in an extended position, wherein the needle 203 occupies at least part of the lumen of the cannula 202 and the needle 203 is positioned to pierce a tissue. The injector device optionally includes a plunger 205 disposed in the lumen defined by the cannula 202. The plunger's shape may vary as long as it fits into the lumen defined by the cannula 202. The injector device may optionally comprise a latch 207, wherein the latch 207 is located on the exterior of the housing 201, the latch 207 is coupled to the shifter 204, and the latch 207 allows a user to retract the needle 203 from the extended position to the retracted position. The injector device may optionally comprise a lip 208 between the proximal end of the cannula 202 and the distal end of the cannula 202. The lip 208 may be configured to impede the cannula 202 from entering a tissue deeper than a length of the cannula 202 distal to the lip 208. The injector device may optionally comprise a payload 206 and a sheath 210 disposed in the lumen of the cannula 202, wherein the sheath 210 slidably engages the cannula 202; in an initial position, the payload 206 is disposed in or adjacent to the sheath 210; and, in an initial position, the sheath 210 is located between an aperture disposed in the cannula 202 and the proximal end of the cannula 202. The injector device optionally comprises a catch 209 disposed in the lumen of the cannula 202, wherein the catch 209 prevents the sheath 210 from advancing through the distal end of the cannula 202.

FIG. 2B depicts an embodiment of the injector device in which the needle 203 is in a retracted position, wherein the distal end of the needle 203 is withdrawn from the lumen of the cannula 202 sufficiently to permit a payload 206 to advance from an initial position through the distal end of the cannula 202. As shown, the injector device includes a housing 201, shifter 204, plunger 205, latch 207, lip 208, catch 209, and sheath 210.

FIG. 2C depicts an embodiment of the injector device in which the needle 203 is in a retracted position, and the plunger 205 has advanced a payload 206 and sheath 210 from an initial position to an intermediate position in the cannula 202. The sheath 210 prevents the payload 206 from entering an aperture disposed in the cannula 202. As shown, the injector device includes a housing 201, shifter 204, latch 207, lip 208, and catch 209.

FIG. 2D depicts an embodiment of the injector device in which the needle 203 is in a retracted position, a sheath 210 is in an intermediate position in the cannula 202, and a plunger 205 has advanced a payload 206 from an initial position through the distal end of the cannula 202. The catch 209 prevents the sheath 210 from advancing through the distal end of the cannula 202. As shown, the injector device includes a housing 201, shifter 204, latch 207, and lip 208.

To use the injector device for delivering the payload into the tissue of a patient, the device is positioned near the desired point of entry into the tissue. The injector device may be mounted on a stand or supported by the hand of a user. The patient will typically be under a topical or local anesthetic. The user can then advance the needle into the tissue and position the cannula at a desired location within the patient's tissue for deposition of the payload. Once the cannula is positioned, the user may prompt the actuator to deliver the payload from the initial position through the lumen and out of the distal end of the cannula. After the payload has been delivered, the cannula is withdrawn from the patient's tissue.

In a preferred embodiment, the injector device is used to deliver a payload into the eye. The injector device may be used to position the payload at a desired implantation site, e.g., in the vitreous cavity of the eye. For such embodiments, the injector device may be positioned near the eye and the needle extended through the sclera and into the vitreous of the eye. The cannula can be positioned at a desired position in the vitreous of the eye for placement of the payload. Once the payload is delivered into the eye, the cannula can be withdrawn.

In certain embodiments, the payload comprises a solid, e.g., an ocular payload such as a drug delivery device. Such devices typically can be delivered into any number of locations in a tissue and can be designed such that a controlled amount of desired drug or therapeutic can be released over time. The payload may comprise a therapeutic agent. The therapeutic agent may comprise a steroid or a biologic. For example, the therapeutic agent may comprise bevacizumab or ranibizumab. In preferred embodiments, the therapeutic agent comprises a corticosteroid, such as fluocinolone acetonide. In some embodiments, the injector device does not comprise a payload, and a payload is supplied by the user prior to use.

In certain embodiments, the payload is a microimplant comprising a therapeutic agent and a polymer. In some embodiments, the microimplant can be delivered through a cannula corresponding to 21-gauge cannula or smaller, and therefore, the microimplant has a cross-sectional diameter of 0.66 mm or less. Methods for making microimplants include extrusion methods, injection molding, compression molding and tableting methods. In certain embodiments, the payload resides in an initial position in the housing of the injector device. In certain embodiments, the payload may be loaded into the housing by the user. The payload may be supplied, for example, in a receptacle, such as a cartridge or ampoule, which may then be loaded into housing. The payload receptacle may be of a single use, refillable, and/or sterilizable.

The needle may comprise metal such as stainless steel. The needle may be 16 gauge to 32 gauge, or smaller. For example, the needle may be 16, 17, 18, 19, 20, 21, 22, 23, 24, 25, 26, 27, 28, 29, 30, 31, 32, 33, or 34 gauge. In preferred embodiments, the needle is 27 gauge. In preferred embodiments, the needle has a beveled tip. The needle may, in some embodiments, create a channel from about 16- to about 32-gauge in the tissue, such as about 25-gauge, about 26-gauge, about 27-gauge about 28-gauge, about 29-gauge or about a 30-gauge channel in the tissue. In preferred embodiments, the needle is flexible such that the needle may exit the lumen of a cannula through an aperture in the wall of the cannula.

In some embodiments, the needle has a non-coring tip. A typical problem when inserting a needle with a lumen into any tissue is the phenomena of "coring" of the tissue, where the insertion actually cuts a cylindrical section of tissue that enters the lumen. Such coring, when it occurs in the eye, can exacerbate leakage of eye fluid through the injection site. An alternative is to use a non-coring needle such as a Tuohy needle, which has a curved tip, or a Huber needle, which has a slanted tip. The proximal end of the needle may comprise a point or a blunt tip. Other traditional methods known in the art for avoiding coring may be used such as deflection of the tip of the needle and sharpening portions of the needle point. Any of these tips may be used interchangeably in the devices disclosed herein, in combination with any other features of the device.

In certain embodiments, the cannula is coupled to the housing of the injector device. The cannula may comprise metal such as stainless steel or a polymeric material such as polyimide, silicone, polycarbonate, and/or polyvinyl carbonate. The cannula may be 15 gauge to 31 gauge, or smaller. The lumen of the cannula must be sufficiently large to allow the needle to occupy at least part of the lumen of the cannula. For example, the cannula may be 15, 16, 17, 18, 19, 20, 21, 22, 23, 24, 25, 26, 27, 28, 29, 30, 31, 32, or 33 gauge. In preferred embodiments, the cannula is 26 gauge. In certain embodiments, cannulas to be used in the present invention are thin-walled. The cannula has an external diameter between 0.25 mm and 1.0 mm, such as approximately 1.0 mm, approximately 0.90 mm, approximately 0.80 mm, approximately 0.70 mm, approximately 0.60 mm, approximately 0.50 mm, approximately 0.40 mm, approximately about 0.30 nun or approximately 0.25 mm. The cannula may, in some embodiments, hold open a channel from about 16- to about 32 gauge in the tissue, such as from about 21- to about 30 gauge in the tissue, such as about 24-gauge, about 25-gauge, about 26-gauge, about 27-gauge, about 28-gauge, about 29-gauge, or about a 30-gauge channel in the tissue. In preferred embodiments, the cannula is straight and linear.

In preferred embodiments, the cannula comprises an aperture located in the wall of the cannula, which permits the needle to exit the lumen of the cannula. In such embodiments, the device may comprise a sheath, configured to prevent the payload from entering or otherwise engaging the aperture. For example, the sheath may frictionally engage the payload such that the sheath advances with the payload as the payload moves from an initial position towards the aperture. Thus, when the sheath and payload reach the aperture, the sheath physically blocks the payload from entering the aperture. In certain such embodiments, the device comprises a catch disposed in the lumen of the cannula, wherein the catch prevents the sheath from exiting the cannula with the payload. Those skilled in the art will recognize that the device may comprise any number of different mechanisms to prevent the sheath from exiting the cannula into the tissue. For example, the lumen of the cannula may be configured such that the internal diameter between the aperture and end of the cannula is smaller than the internal diameter of the rest of the cannula such that the smaller internal diameter obstructs the sheath from exiting the cannula.

The cannula of the invention may have a uniform external diameter or the diameter may vary along the length of the cannula. In some embodiments, the device comprises a stop disposed on the cannula. The device may comprise a positive stop. For example, as in FIG. 2, the cannula 202 may have a lip 208 and the cannula 202 may advance into a tissue until the lip 208 meets the tissue, such that the lip 208 hinders further advancement of the cannula 202 into the tissue (FIG. 2). In other exemplary embodiments, the device may comprise a negative stop. For example, the cannula may have a section of contracted diameter relative to other portions of the cannula in which the cannula may advance into the tissue until the cannula's contracted diameter section meets the tissue and hinders further advancement and/or retraction into and/or from the tissue (See, e.g., U.S. Pat. No. 8,192,408, incorporated by reference). In certain such embodiments, the stop may correspond to a predetermined depth of entry into the tissue or a desired implantation depth.

The invention further contemplates the use of cannulas having non-circular cross-sections, including oval or elliptical cross-sections. For such non-circular cross-sectional cannulas, it is desirable that the cross-sectional area correspond to that of a circular cannula having up to a 1.0 mm diameter.

In certain embodiments, the cannula is designed to limit the introduction of air into the tissue upon injection of the payload. In an exemplary embodiment, the payload can be positioned proximally to the cannula tip but with sufficient tolerance between the payload and cannula wall to provide for air exhaust past the payload as it is moved through the cannula displacing the air in front of it.

The payload may then be advanced into the tissue by any means such as a plunger, a pump, vibration, or an electrostatic gradient. The actuator is preferably a plunger. The plunger is preferably linear. In preferred embodiments, the cannula and plunger are both linear and the plunger and cannula are coaxially aligned. In certain embodiments, wherein the payload is advanced by a plunger, the plunger may be actuated by any means such as by a spring, compressed gas, or manual compression. In some embodiments, the payload is advanced by a spring and the spring is a tension spring, compression spring, or torsion spring.

Additional embodiments provide for safety features which include, among other things, locking mechanisms, which deter reuse of the injector device, gauges to determine the location of the proximal end of the cannula within the tissue, and pressure gauges to monitor pressure build-up within the tissue, such as the eye.

In addition to delivering payloads into the eye, devices as disclosed herein can be used to inject payloads into other tissues, and these devices are of particular use where minimal tissue damage is desired, e.g., implantation into the cerebrospinal fluid, the bladder, etc.

In some aspects, the invention relates to an injector device, comprising a housing; a cannula defining a lumen and having a proximal end received in the housing and a distal end extending from the housing; a hollow needle comprising a distal end with a tip for piercing tissue; a shifter that shifts the needle from an extended position to a retracted position; and an actuator for advancing a payload from an initial position to exit from the distal end of the cannula. In an extended position, the needle may occupy at least part of the lumen of the cannula, and the distal end of the needle extends past the distal end of the cannula. In a retracted position, the distal end of the needle may be withdrawn from the lumen of the cannula sufficiently to permit a payload to advance from an initial position through the distal end of the cannula.

The injector device may comprise a payload, wherein the payload comprises a therapeutically effective amount of one or more drugs. The one or more drugs may comprise a steroid, such as fluocinolone acetonide, or a biologic, such as bevacizumab or ranibizumab.

In some embodiments, the needle is 16 gauge to 32 gauge, or smaller. In preferred embodiments, the needle is 27 gauge. The needle may have a beveled tip. The needle may have a non-coring tip. In some embodiments, the needle comprises metal, such as stainless steel. The needle may slidably engage the cannula walls when the needle is in the lumen of the cannula.

In some embodiments, the cannula is 15 gauge to 31 gauge, or smaller. In preferred embodiments, the cannula is 26 gauge. The cannula may comprise metal, such as stainless steel. The cannula may comprise a polymeric material, such as polyimide or polycarbonate. The cannula may be linear.

In some embodiments, the injector device comprises a stop disposed on the cannula. The stop may comprise a lip between the proximal end of the cannula and the distal end of the cannula; and the lip may be configured to impede the cannula from entering a tissue deeper than a length of the cannula distal to the lip.

In certain embodiments, the injector device comprises a latch, wherein the latch is located on the exterior of the housing; the latch is coupled to the shifter; and the latch allows a user to retract the needle from the extended position to the retracted position.

In some embodiments, the injector device comprises an aperture in the cannula, wherein the aperture is located in a wall of the cannula between the proximal end of the cannula and the distal end of the cannula; and the device is configured so that, in the extended position, the needle extends through the aperture, and when the needle is shifted from the extended position to the retracted position, the tip of the needle exits the lumen of the cannula through the aperture.

In certain embodiments, the injector device comprises a payload and a sheath disposed in the lumen of the cannula, wherein the sheath slidably engages the cannula; in an initial position, the payload is disposed in or adjacent to the sheath; in an initial position, the sheath is located between the aperture and the proximal end of the cannula; and when the tip of the needle exits the lumen of the cannula through the aperture, the sheath can advance to prevent the payload from entering the aperture. The sheath may frictionally engage the payload in an initial position. The sheath may disengage the payload before the payload advances through the distal end of the cannula.

In some embodiments, the injector device comprises a catch disposed in the lumen of the cannula, wherein the catch prevents the sheath from advancing through the distal end of the cannula and allows the payload to advance through the distal end of the cannula, thereby causing the sheath to disengage the payload. The catch may be located between the aperture and the distal end of the cannula.

In certain embodiments, the lumen of the cannula comprises a first internal diameter between the initial position of the payload and the aperture; the sheath is disposed in the lumen of the cannula having the first internal diameter; the lumen of the cannula comprises a second internal diameter between the aperture and the distal end of the cannula; the second internal diameter is smaller than the first internal diameter; and the second internal diameter does not accommodate the sheath, thereby preventing the sheath from advancing through the distal end of the cannula. The first internal diameter may slidably engage the sheath.

In some embodiments, the actuator is a plunger or pump. In preferred embodiments, the actuator is a plunger. In certain embodiments, the actuator is a plunger and the plunger is actuated by compressed gas or an elastic material, such as a spring. The spring may be, for example, a tension spring, compression spring, or torsion spring. In some embodiments, the actuator is a plunger and the plunger is linear. In certain embodiments cannula is linear and the plunger and the cannula are coaxially aligned.

In some embodiments, the tissue comprises an eye.

In certain aspects, the invention relates to a method for delivering a payload to a tissue comprising piercing the tissue with the distal end of the needle of the injector device; piercing the tissue with the distal end of the cannula; retracting the needle to a retracted position while maintaining the distal end of the cannula in the tissue; advancing a payload through the distal end of the cannula into the tissue; and removing the cannula from the tissue.

The injector device may be stored with the needle partially retracted, for example, to prevent damage to the needle. Thus, in some embodiments, the method comprises shifting the needle into the extended position prior to piercing the tissue.

In certain aspects, piercing the tissue with the distal end of the cannula comprises advancing the cannula into the tissue until a surface of the tissue contacts a stop disposed on the cannula. In some embodiments, advancing the cannula into the tissue until a surface of the tissue contacts a stop disposed on the cannula comprises advancing the cannula into the tissue until a surface of the tissue contacts a lip disposed on the cannula.

In some embodiments, retracting the needle comprises shifting the shifter from an initial position to a final position. The injector device may comprise a latch, and retracting the needle comprises shifting the latch from an initial position to a final position. In preferred embodiments, retracting the needle comprises retracting the needle through an aperture located in the wall of the cannula.

In some embodiments, the method comprises advancing a sheath from an initial position to a final position blocking the aperture. The method may comprise advancing the sheath from the initial position to a final position blocking the aperture comprises advancing in tandem both the sheath and the payload from the initial position to a final position where the sheath covers the aperture. Advancing the sheath may comprise advancing the sheath to engage a catch that blocks the sheath from progressing farther down the lumen at a point where the sheath is blocking the aperture. In certain embodiments, the method comprises advancing the payload along the sheath past the catch and through the distal end of the needle.

In some embodiments, delivering a payload to a tissue comprises delivering a payload to the eye.

Equivalents

The present invention provides, among other things, injector assemblies and methods of use thereof. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

We claim:

1. An injector device, comprising:
    a housing;
    a cannula defining a lumen and having a proximal end received in the housing and a distal end extending from the housing; wherein the cannula further comprises an aperture that is located in a wall of the cannula between the proximal end of the cannula and the distal end of the cannula;
    a hollow needle comprising a distal end with a tip for piercing a tissue;
    a shifter that shifts the needle from an extended position to a retracted position; and
    an actuator for advancing a payload from an initial position to exit from the distal end of the cannula,
    wherein the device is configured so that, in the extended position, the needle extends through the aperture and occupies at least part of the lumen of the cannula, and the distal end of the needle extends past the distal end of the cannula;

wherein, when the needle is shifted from the extended position to the retracted position, the tip of the needle exits the lumen of the cannula through the aperture, and
wherein, in the retracted position, the distal end of the needle is withdrawn from the lumen of the cannula sufficiently to permit the payload to advance from the initial position through the distal end of the cannula.

2. The injector device of claim 1, further comprising the payload, wherein the payload comprises a therapeutically effective amount of one or more drugs.

3. The injector device of claim 2, wherein the one or more drugs comprise a steroid or a biologic.

4. The injector device of claim 3, wherein the one or more drugs comprise the steroid and the steroid is fluocinolone acetonide.

5. The injector device of any one of the preceding claims, wherein the needle is 16 gauge to 32 gauge, or smaller.

6. The injector device of claim 5, wherein the needle is 27 gauge.

7. The injector device according to claim 1, wherein the tip of the needle is a beveled tip.

8. The injector device according to claim 1, wherein the tip of the needle is a non-coring tip.

9. The injector device according to claim 1, wherein the needle comprises metal.

10. The injector device of claim 9, wherein the needle comprises stainless steel.

11. The injector device according to claim 1, wherein the needle slidably engages walls of the cannula when the needle is in the lumen of the cannula.

12. The injector device according to claim 1, wherein the cannula is 15 gauge to 31 gauge, or smaller.

13. The injector device of claim 12, wherein the cannula is 26 gauge.

14. The injector device according to claim 1, wherein the cannula comprises metal.

15. The injector device of claim 14, wherein the cannula comprises stainless steel.

16. The injector device according to claim 1, wherein the cannula comprises a polymeric material.

17. The injector device of claim 16, wherein the cannula comprises polyimide or polycarbonate.

18. The injector device according to claim 1, wherein the cannula is linear.

19. The injector device according to claim 1, further comprising a stop disposed on the cannula.

20. The injector device of claim 19, wherein: the stop comprises a lip between the proximal end of the cannula and the distal end of the cannula; and the lip is configured to impede the cannula from entering the tissue deeper than a length of the cannula distal to the lip.

21. The injector device according to claim 1, further comprising a latch, wherein:
the latch is located on an exterior of the housing;
the latch is coupled to the shifter; and
the latch allows a user to retract the needle from the extended position to the retracted position.

22. The injector device of claim 1, further comprising the payload and a sheath disposed in the lumen of the cannula, wherein:
the sheath slidably engages the cannula;
in the initial position, the payload is disposed in or adjacent to the sheath;
in the initial position, the sheath is located between the aperture and the proximal end of the cannula; and
when the tip of the needle exits the lumen of the cannula through the aperture, the sheath can advance to prevent the payload from entering the aperture.

23. The injector device of claim 22, wherein the sheath frictionally engages the payload in the initial position.

24. The injector device of claim 23, wherein the sheath disengages the payload before the payload advances through the distal end of the cannula.

25. The injector device of claim 24, further comprising a catch disposed in the lumen of the cannula, wherein the catch prevents the sheath from advancing through the distal end of the cannula and allows the payload to advance through the distal end of the cannula, thereby causing the sheath to disengage the payload.

26. The injector device of claim 25, wherein the catch is located between the aperture and the distal end of the cannula.

27. The injector device according to claim 22, wherein:
the lumen of the cannula comprises a first internal diameter between the initial position of the payload and the aperture;
the sheath is disposed in the lumen of the cannula having the first internal diameter;
the lumen of the cannula comprises a second internal diameter between the aperture and the distal end of the cannula;
the second internal diameter is smaller than the first internal diameter; and
the second internal diameter does not accommodate the sheath, thereby preventing the sheath from advancing through the distal end of the cannula.

28. The injector device of claim 27, wherein the first internal diameter slidably engages the sheath.

29. The injector device according to claim 1, wherein the actuator is a plunger or a pump.

30. The injector device of claim 29, wherein the actuator is the plunger.

31. The injector device of claim 30, wherein the plunger is actuated by a compressed gas or an elastic material.

32. The injector device of claim 31, wherein the plunger is actuated by the elastic material and the elastic material is a spring.

33. The injector device of claim 32, wherein the spring is a tension spring, a compression spring, or a torsion spring.

34. The injector device according to claim 30, wherein the plunger is linear.

35. The injector device of claim 34, wherein the cannula is linear and the plunger and the cannula are coaxially aligned.

36. The injector device according to claim 1, wherein the tissue comprises an eye.

37. A method for delivering a payload to a tissue comprising:
piercing the tissue with the distal end of the needle of the injector device according to claim 1;
piercing the tissue with the distal end of the cannula;
retracting the needle to the retracted position while maintaining the distal end of the cannula in the tissue;
advancing the payload through the distal end of the cannula into the tissue; and
removing the cannula from the tissue.

38. The method of claim 37, further comprising shifting the needle into the extended position prior to piercing the tissue.

39. The method of claim 37, wherein piercing the tissue with the distal end of the cannula comprises advancing the cannula into the tissue until a surface of the tissue contacts a stop disposed on the cannula.

40. The method of claim 39, wherein advancing the cannula into the tissue until the surface of the tissue contacts the stop disposed on the cannula comprises advancing the cannula into the tissue until the surface of the tissue contacts a lip disposed on the cannula.

41. The method according to claim 37, wherein retracting the needle comprises shifting the shifter from an initial position to a final position.

42. The method according to claim 37, wherein the injector device comprises a latch, and retracting the needle comprises shifting the latch from an initial position to a final position.

43. The method according to claim 37, wherein retracting the needle comprises retracting the needle through the aperture located in the wall of the cannula.

44. The method of claim 43, further comprising advancing a sheath from an initial position to a final position blocking the aperture.

45. The method according to claim 44 wherein advancing the sheath from the initial position to the final position blocking the aperture comprises advancing in tandem both the sheath and the payload from the initial positions of the sheath and the payload to the final position where the sheath covers the aperture.

46. The method according to claim 44, wherein advancing the sheath comprises advancing the sheath to engage a catch that blocks the sheath from progressing farther down the lumen at a point where the sheath is blocking the aperture.

47. The method of claim 46, further comprising advancing the payload along the sheath past the catch and through the distal end of the needle.

48. The method according to claim 37, wherein advancing the payload into the tissue comprises delivering the payload to an eye.

* * * * *